(12) United States Patent
Axelsson et al.

(10) Patent No.: US 8,128,275 B2
(45) Date of Patent: Mar. 6, 2012

(54) DEVICE AT BONE CEMENT MIXER

(75) Inventors: Fredrik Axelsson, Malmö (SE); Ronny Bengtsson, Kristianstad (SE); Lars Wilander, Örkelljunga (SE)

(73) Assignee: Biomet Cementing Technologies AB, Sjobo (SE)

( * ) Notice: Subject to any disclaimer, the term of this patent is extended or adjusted under 35 U.S.C. 154(b) by 762 days.

(21) Appl. No.: 11/881,008

(22) Filed: Jul. 25, 2007

(65) Prior Publication Data

US 2008/0037362 A1 Feb. 14, 2008

(30) Foreign Application Priority Data

Aug. 11, 2006 (SE) ........................................ 0601668

(51) Int. Cl.
*B01F 13/00* (2006.01)
*B01F 11/00* (2006.01)

(52) U.S. Cl. ........................................ 366/130; 366/333
(58) Field of Classification Search .................. 366/130, 366/333
See application file for complete search history.

(56) References Cited

U.S. PATENT DOCUMENTS

| | | | |
|---|---|---|---|
| 5,370,221 A | 12/1994 | Magnusson et al. | |
| RE35,276 E * | 6/1996 | Chan | 366/139 |
| 5,549,380 A | 8/1996 | Lidgren et al. | |
| 5,551,778 A | 9/1996 | Hauke et al. | |
| 5,588,745 A | 12/1996 | Tanaka et al. | |
| 5,634,714 A * | 6/1997 | Guild | 366/130 |
| 5,857,771 A | 1/1999 | Draenert | |
| 6,312,149 B1 | 11/2001 | Sjovall et al. | |
| 6,481,435 B2 * | 11/2002 | Hochrainer et al. | 128/200.14 |
| 6,635,044 B2 * | 10/2003 | Lopez | 604/500 |
| 2002/0191487 A1 | 12/2002 | Sand | |
| 2004/0066706 A1 | 4/2004 | Barker et al. | |
| 2004/0196735 A1 | 10/2004 | Barker et al. | |

FOREIGN PATENT DOCUMENTS

| | | |
|---|---|---|
| EP | 1 466 572 A2 | 10/2004 |
| WO | WO 97/18031 A1 | 5/1997 |
| WO | WO 2004/103541 A1 | 12/2004 |
| WO | WO 2005/096970 A2 | 10/2005 |
| WO | WO 2006/023430 A2 | 3/2006 |

* cited by examiner

*Primary Examiner* — Walter D Griffin
*Assistant Examiner* — Christopher Vandeusen
(74) *Attorney, Agent, or Firm* — Tarolli, Sundheim, Covell & Tummino LL (57) ABSTRACT

A bone cement mixer includes one mixing space (5) for mixing powder and liquid components (2, 4) to make bone cement. The powder component (2) is placed in the mixing space (5) and the liquid component (4) in a liquid container (3). The liquid container (3) may be an aerosol container (15) and contains, in addition to the liquid component (4), a propellant gas for pushing the liquid component (4) out from the aerosol container (15) into the mixing space (5). The aerosol container (15) has a connecting element (16) for connecting it to the bone cement mixer (1), and it is closed and adapted to being opened when it is connected to a corresponding connecting element (17) on the bone cement mixer (1), so that the liquid component (4) is pushed out from the aerosol container (15) into the mixing space (5) by the propellant gas.

29 Claims, 8 Drawing Sheets

DEVICE AT BONE CEMENT MIXER

FIELD OF THE INVENTION

The present invention relates to a device at a bone cement mixer, wherein the bone cement mixer comprises at least one mixing space for mixing a powder component and a liquid component, preferably a polymer and a monomer respectively, to make bone cement, wherein the powder component is placed in the mixing space and the liquid component in a liquid container, and wherein the liquid component can be transferred from the liquid container to the mixing space and the powder component placed therein.

BACKGROUND OF THE INVENTION

A known practice is for the liquid component to be transferred from the liquid container to the mixing space in the bone cement mixer by being sucked out from the liquid container into the mixing space. This entails suction by means of vacuum generated in the mixing space by a suction source connected to the bone cement mixer.

Although such vacuum suction has been found to work satisfactorily, it is possible to speed up and improve the mixing of the powder and liquid components.

SUMMARY OF THE INVENTION

It is therefore an object of the invention to achieve quicker controllable and better dispersion of the liquid component in the powder component and hence quicker controllable and better mutual mixing of them. This object is achieved according to the invention by the device mainly comprising the characterizing features indicated in claim 1 below.

The desired quicker controllable and better dispersion of the liquid component in the powder component and hence quicker and better mixing of them is primarily achieved by the liquid container being an aerosol container which contains, in addition to the liquid component, a propellant gas which, when the liquid container is connected to the bone cement mixer, pushes the liquid component out from the aerosol container into the mixing space in the bone cement mixer.

Moreover, according to the invention, the design is made simpler and more reliable by the liquid container and the bone cement mixer each having a mutually appropriate connecting element.

WO 2005096970 A2 describes inter alia a liquid container and a container for powder. The liquid container may contain a pressure gas for pushing the liquid out from the liquid container. In the arrangement according to that publication, in contrast with the present invention, there is a separate element for connection to the liquid container and to the mixing container so that a connection is formed between these containers. This separate element has an opening means which acts in two opposite directions and which is therefore configured accordingly to make this possible. The opening means is not situated on the mixing container or its connecting element.

BRIEF DESCRIPTION OF THE DRAWINGS

The invention is described in more detail with reference to the attached drawings, in which.

DESCRIPTION OF EXAMPLE EMBODIMENTS

The drawings depict a bone cement mixer 1 containing a powder component 2, preferably a polymer. It also depicts a liquid container 3 containing a liquid component 4, preferably a monomer.

The bone cement mixer 1 chosen by way of example is of a type similar to that referred to in U.S. Pat. No. 5,549,380. Thus the bone cement mixer 1 has a mixing space 5 in which there is a powder component 2. Said bone cement mixer 1 also comprises a mixing means 6 which may be operable manually in order to mix the powder and liquid components 2, 4 situated in the mixing space 5 in order to make bone cement 7. The bone cement mixer 1 also comprises a delivery means 8 in the form of a piston which can in a known manner be anchored to the bone cement mixer in order to be held in position during the mixing of the powder and liquid components 2, 4. The delivery piston 8 can also in a known manner be released from the bone cement mixer 1 to allow it to be pressed by a delivery tool P into the mixing space 5 in order to deliver ready-mixed bone cement 7 from the latter.

The bone cement mixer 1 is connectable to a vacuum source 9 adapted to generate vacuum in the mixing space 5 during mixing of the powder and liquid components 2, 4, and the vacuum is preferably maintainable during subsequent accumulation of ready-mixed bone cement 7 in a delivery portion 10 of the mixing space 5. The vacuum source 9 is intended to generate such vacuum in the mixing space 5 that the porosity of the bone cement 7 is reduced or eliminated. For accumulation of bone cement 7, the vacuum source 9 is also adapted to sucking the delivery piston 8 towards the delivery portion 10 in order to accumulate bone cement 7 in the latter. The delivery portion 10 has a nipple 11 or equivalent to which a hose 33 or equivalent from the vacuum source 9 is connectable in order to connect the bone cement mixer 1 to the vacuum source 9.

A filter 12 may be disposed in the delivery portion 10 within and/or around the nipple 11 in order to prevent powder or liquid components 2, 4 or bone cement 7 from being sucked out of the mixing space 5.

Figure 11:
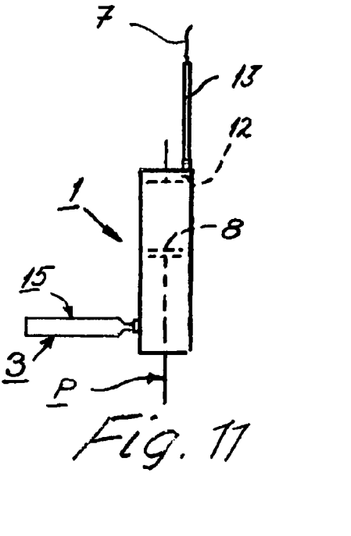
FIG. 11 depicts the bone cement mixer during delivery of bone cement from it.

When bone cement 7 has been made in the bone cement mixer 1, the hose 33 from the vacuum source 9 is disconnected and a delivery pipe 13 is connected to the nipple 11. Thereafter, the delivery piston 8 with the feed tool P is pushed towards the delivery portion 10, thereby delivering the ready-mixed bone cement 7 via the delivery pipe 13 (FIG. 11).

The liquid component 4 is in a liquid container 3 configured as an aerosol container 15 made of such glass, plastic or metal material, e.g. aluminum or an aluminum alloy, that its walls prevent the liquid component from escaping from it. The aerosol container 15 contains, in addition to the liquid component 4, a propellant gas for pushing the liquid component out from the aerosol container into the mixing space 5 in the bone cement mixer 1. The aerosol container 15 has a connecting element 16 for connecting it to the bone cement mixer 1, and this connecting element 16 is adapted to being opened when it is connected to a corresponding connecting element 17 on the bone cement mixer 1. When the aerosol container 15 is opened by being connected to the bone cement mixer 1, the liquid component 4 is pushed out of the aerosol container into the mixing space 5 (arrows A) by the propellant gas (arrows B in FIGS. 4 to 9) in the aerosol container. The fact that vacuum preferably prevails in the mixing space 5 and the pressure difference between the mixing space and the aerosol container 15 is therefore greater than when using a liquid container 3 of some other type results in the transfer of the liquid component from the aerosol container to the mixing space being still quicker than has previously been possible. The pressure difference nevertheless allows a controlled rate of transfer of the liquid component to the mixing space.

In the embodiments depicted, the mixing space 5 in the bone cement mixer 1, which is shown as elongate, and the bone cement mixer's connecting element 17 are disposed radially relative to the longitudinal axis of the mixing space.

The connecting element 16 of the aerosol container 15 and the corresponding connecting element 17 on the bone cement mixer 1 in the embodiments according to FIGS. 2 and 3 and FIGS. 4, 5 and 6 are designed to form together a threaded joint. For this purpose, the connecting element 16 of the aerosol container 15 is preferably cylindrical and has threads, preferably outside threads 19, which make it possible for it to be screwed firmly to threads, preferably inside threads 20, on the corresponding preferably cylindrical connecting element 17 on the bone cement mixer 1. Alternatively, said connecting elements 16, 17 may together form a snap joint (FIGS. 7, 8 and 9), for which purpose the connecting element 17 of the bone cement mixer 1 may for example have a flange 28 pointing radially inwards which is fastenable by being snapped into a groove 30 delineated between flanges 29 pointing radially outwards on the corresponding connecting element 16 on the aerosol container 15. According to another alternative embodiment (not depicted) said connecting elements 16, 17 may together form a bayonet joint. Other types of connection between the connecting elements 16, 17 are also possible.

The connecting element 16 of the aerosol container 15 has a closing wall 21 which closes it. The closing wall 21 is openable by at least one opening means 22 on the bone cement mixer 1 when the connecting element 16 of the aerosol container 15 is connected, in the embodiment depicted, by being screwed firmly or snapped on, to the bone cement mixer's connecting element 17. The closing wall 21 comprises with advantage a material readily penetrable by the opening means 22, e.g. it comprises an elastic material such as rubber or soft plastic or, for example, a penetrable metal foil. In the case of an aerosol container 15 made of plastic or metal, the closing wall 21 may also with advantage comprise thinner portions of the container material. The opening means 22 is so configured or disposed as to allow the propellant gas in the aerosol container 15 to push the liquid component 4 out from the aerosol container 15 past (FIG. 3) or through (FIGS. 6 and 9) the opening means and into the mixing space. In the embodiments depicted, the opening, means 22 is disposed in the connecting element 17 of the bone cement mixer 1 so that it pushes up at least one hole in the closing wall 21 of the aerosol container 15 when the latter's connecting element 16 is connected, preferably by being screwed firmly or snapped on, to the connecting element 17 of the bone cement mixer. The opening means 22 is configured substantially as a needle 24 in FIGS. 2 and 3 and substantially as a cannula 25 in FIGS. 4 to 9, but may be of any suitable shape.

Figure 2:
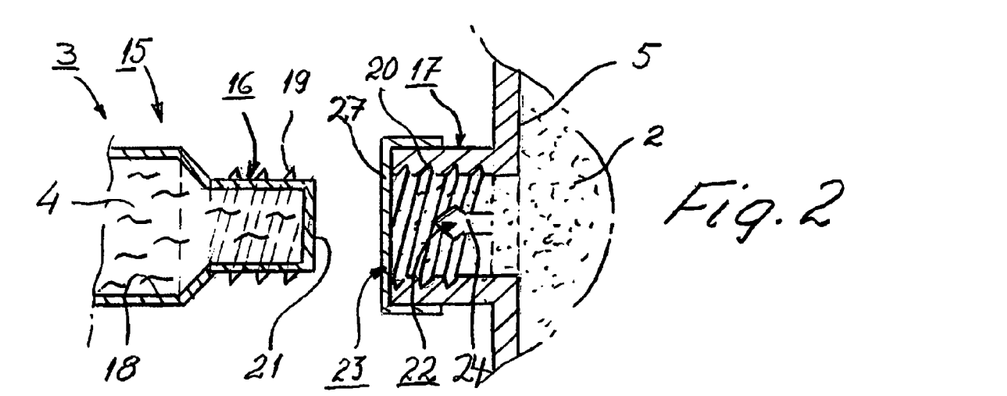
FIGS. 2 and 3 are sections through a first embodiment of a connecting element on the liquid container and through a corresponding connecting element on the bone cement mixer before and after their connection to one another.
Figure 3:
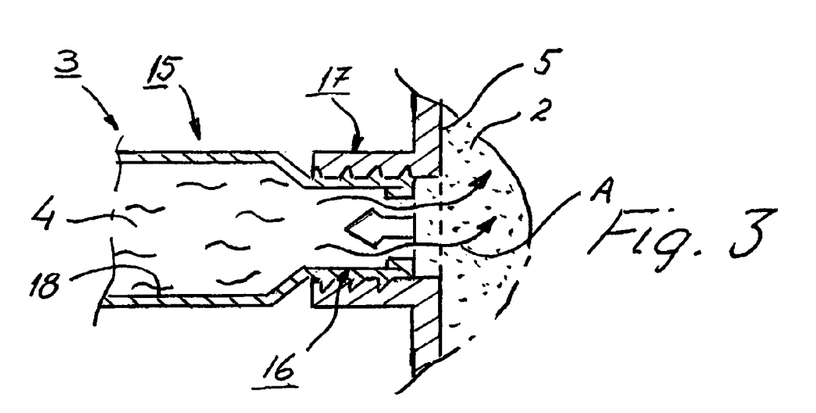
Figure 4:
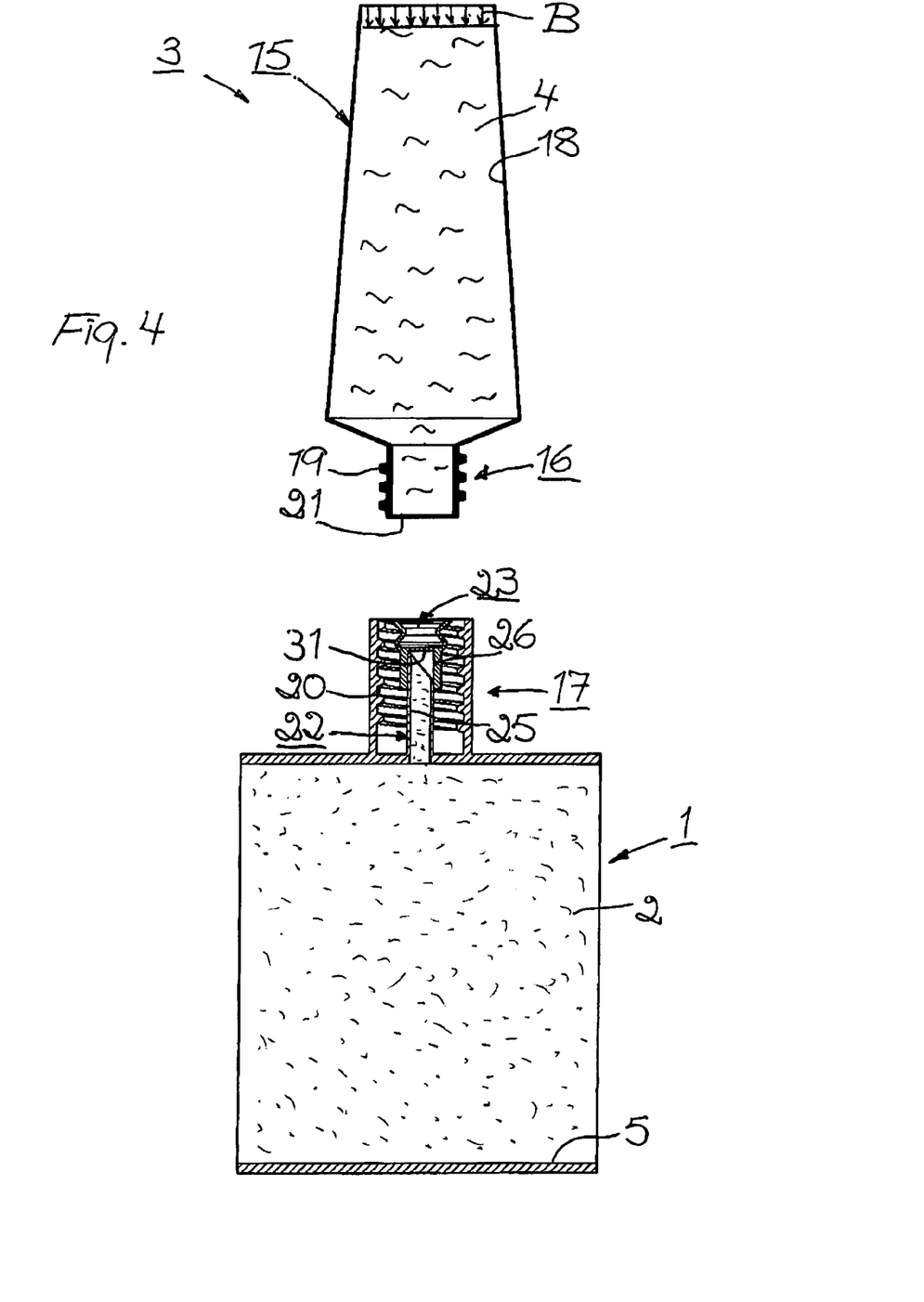
FIGS. 4, 5 and 6 are sections through, inter alia, a second embodiment of a connecting element on the liquid container and through a corresponding connecting element on the bone cement mixer before, during and after their connection to one another.
Figure 5:
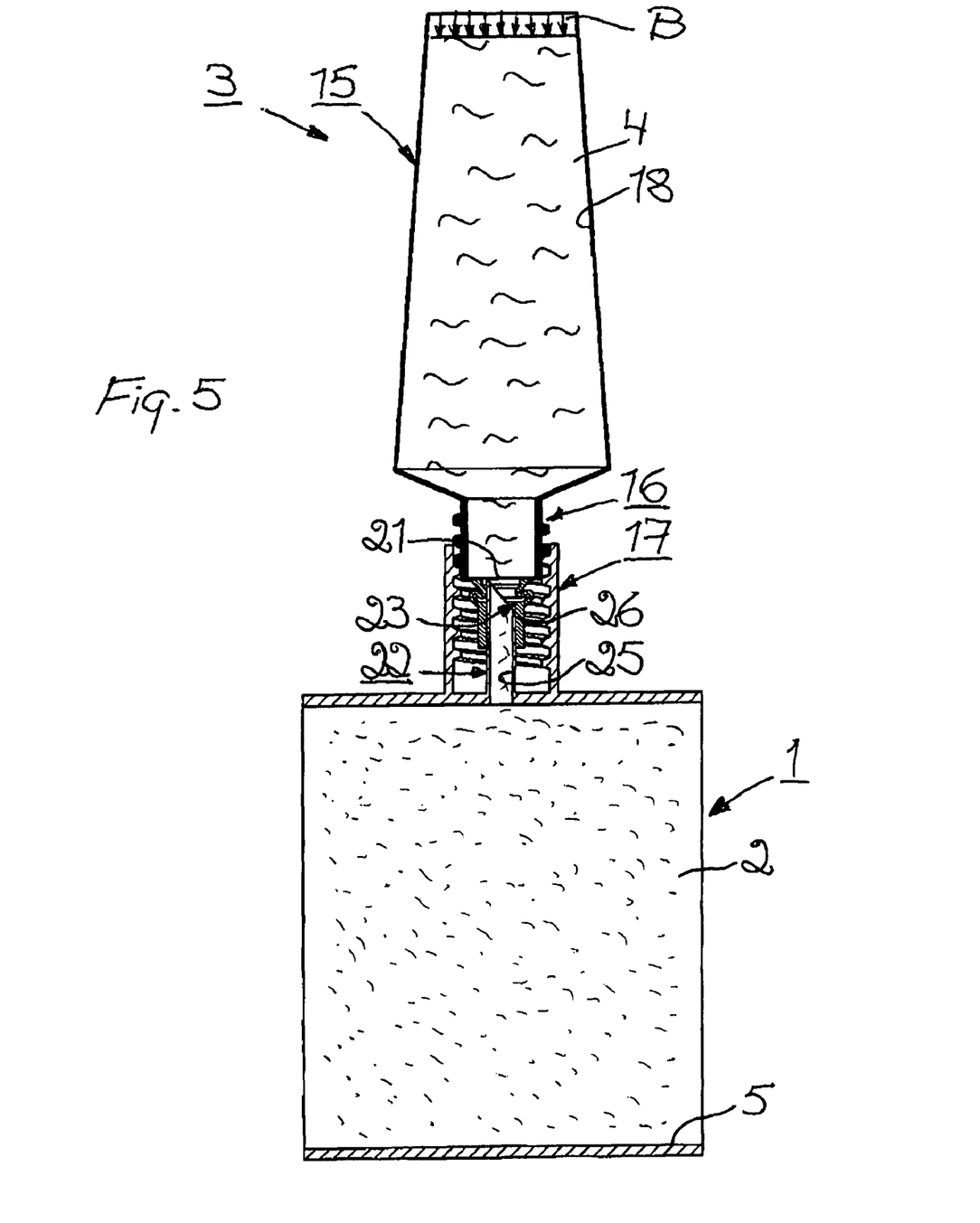
Figure 6:
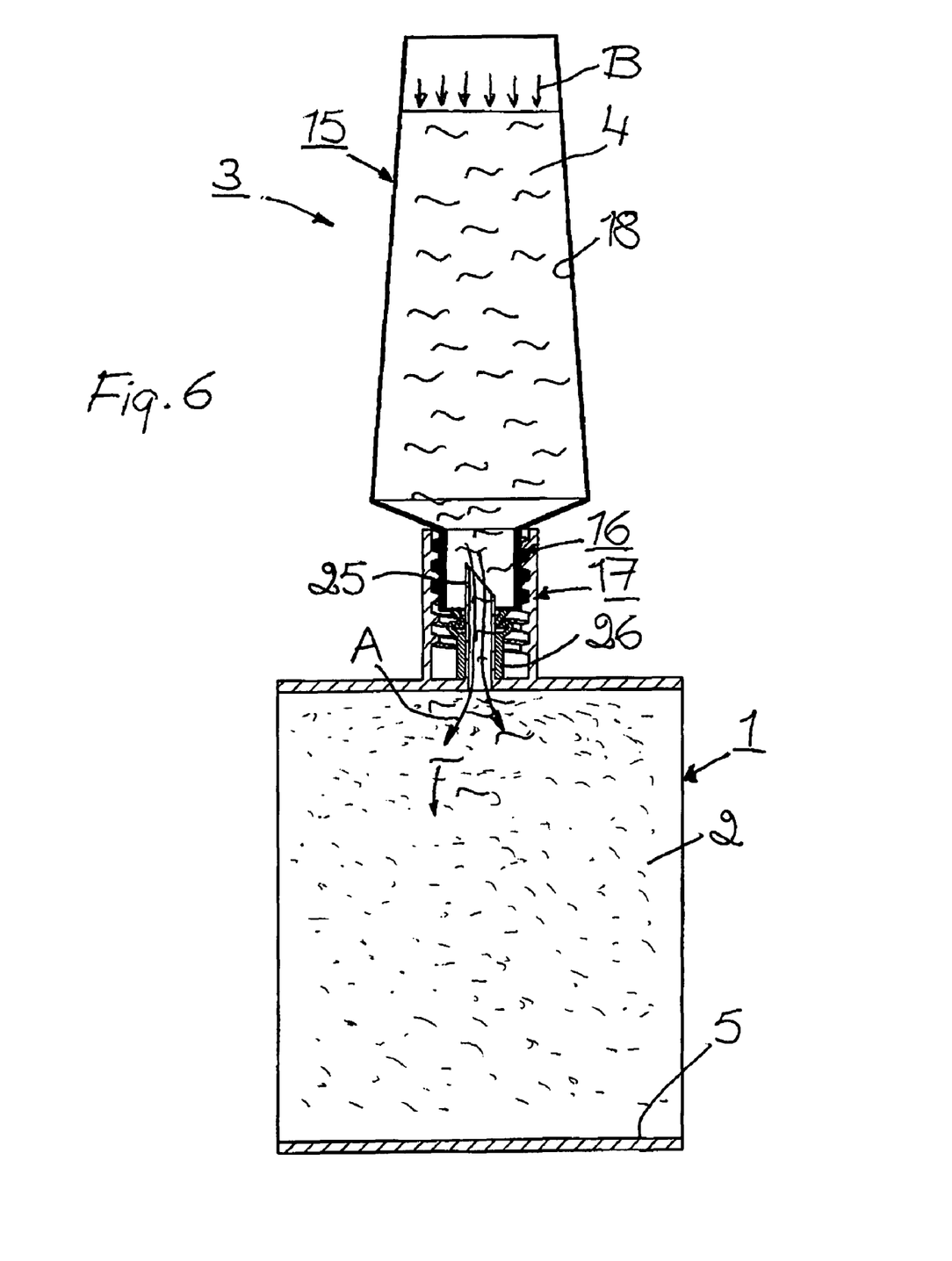

With a view to ensuring that the powder component 2 remains in the mixing space 5 of the bone cement mixer 1 and preventing its running out before the liquid component 4 is supplied as a result of cessation of vacuum therein, the connecting element 17 of the bone cement mixer has a seal 23 which closes this space. The seal 23 according to FIG. 2 is configured as a manually removable cap 27. The seal 23 according to FIGS. 4 to 9, in order to maintain the vacuum in the mixing space 5 of the bone cement mixer 1 until connection has been effected, is in this case openable by the opening means 22 when the connecting element 16 of the aerosol container 15 is connected, in the embodiments depicted, by being screwed firmly or snapped on, to the connecting element 17 of the bone cement mixer 1. According to FIGS. 4 to 9, the opening means 22 takes the form, as indicated above, of a cannula 25 and the seal 23 takes the form of a rubber socket 26 placed over at least the tip of the cannula, whereby the cannula pushes up first a hole in a sealing wall 31 of the rubber socket and thereafter a hole in the closing wall 21 of the connecting element 16 of the aerosol container 15 when the connecting element of the aerosol container is connected, in the embodiments depicted, by being screwed firmly or snapped on, to the connecting element 17 of the bone cement mixer 1. Other types of seals 23 are also possible.

Figure 7:
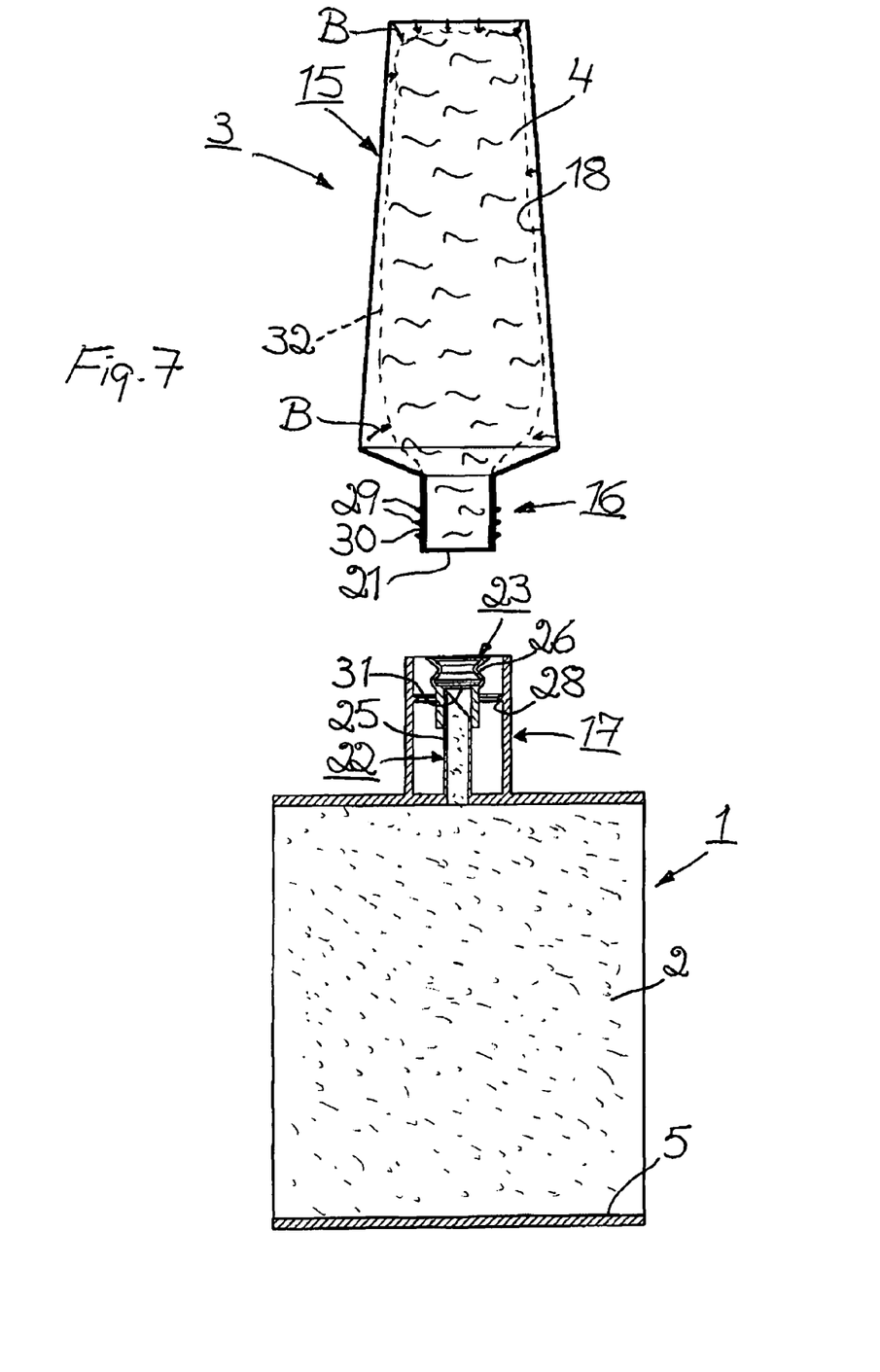
FIGS. 7, 8 and 9 are sections through, inter alia, a third embodiment of a connecting element on another type of liquid container and through a corresponding connecting element on the bone cement mixer before, during and after their connection to one another.
Figure 8:
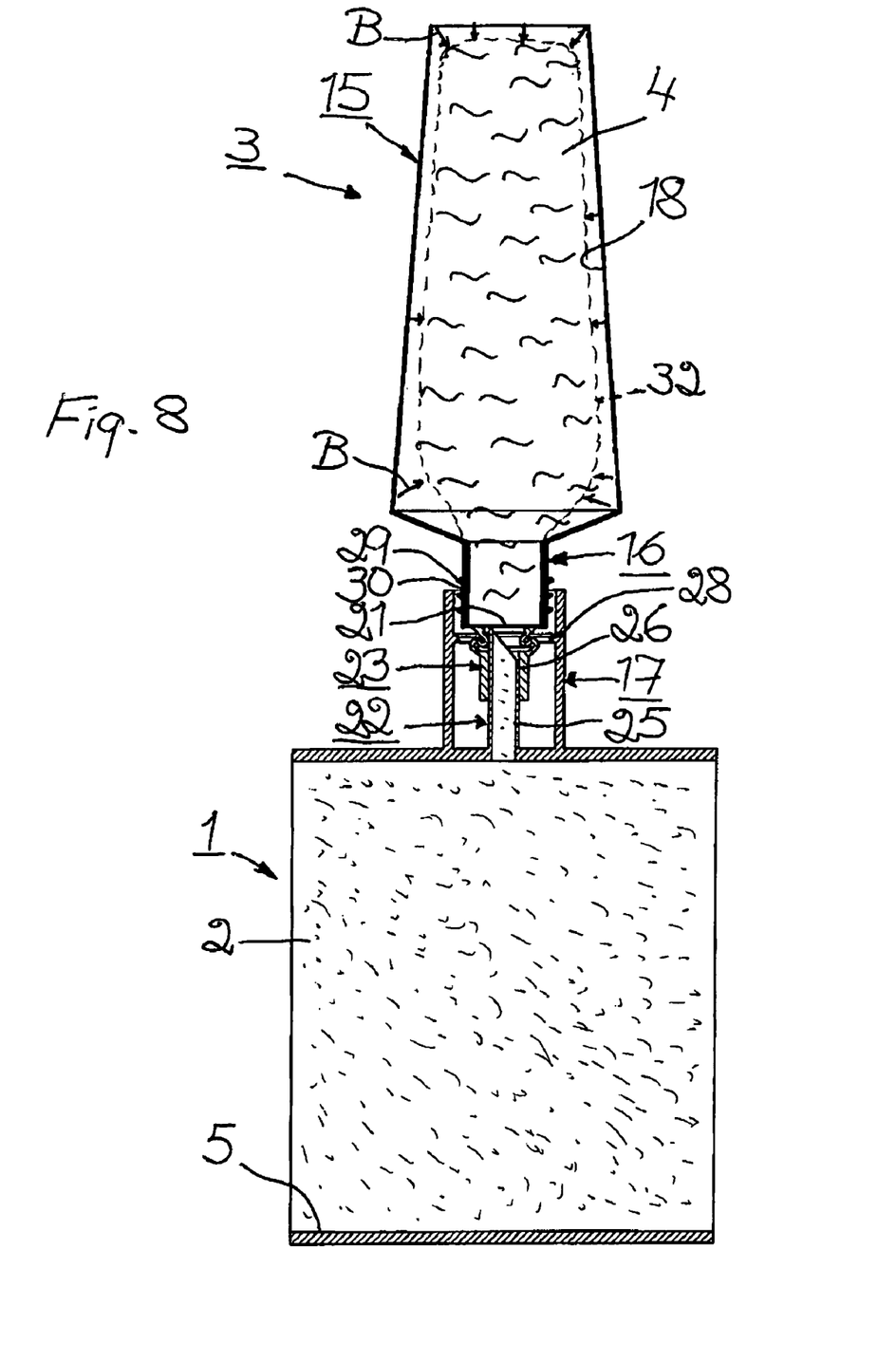
Figure 9:
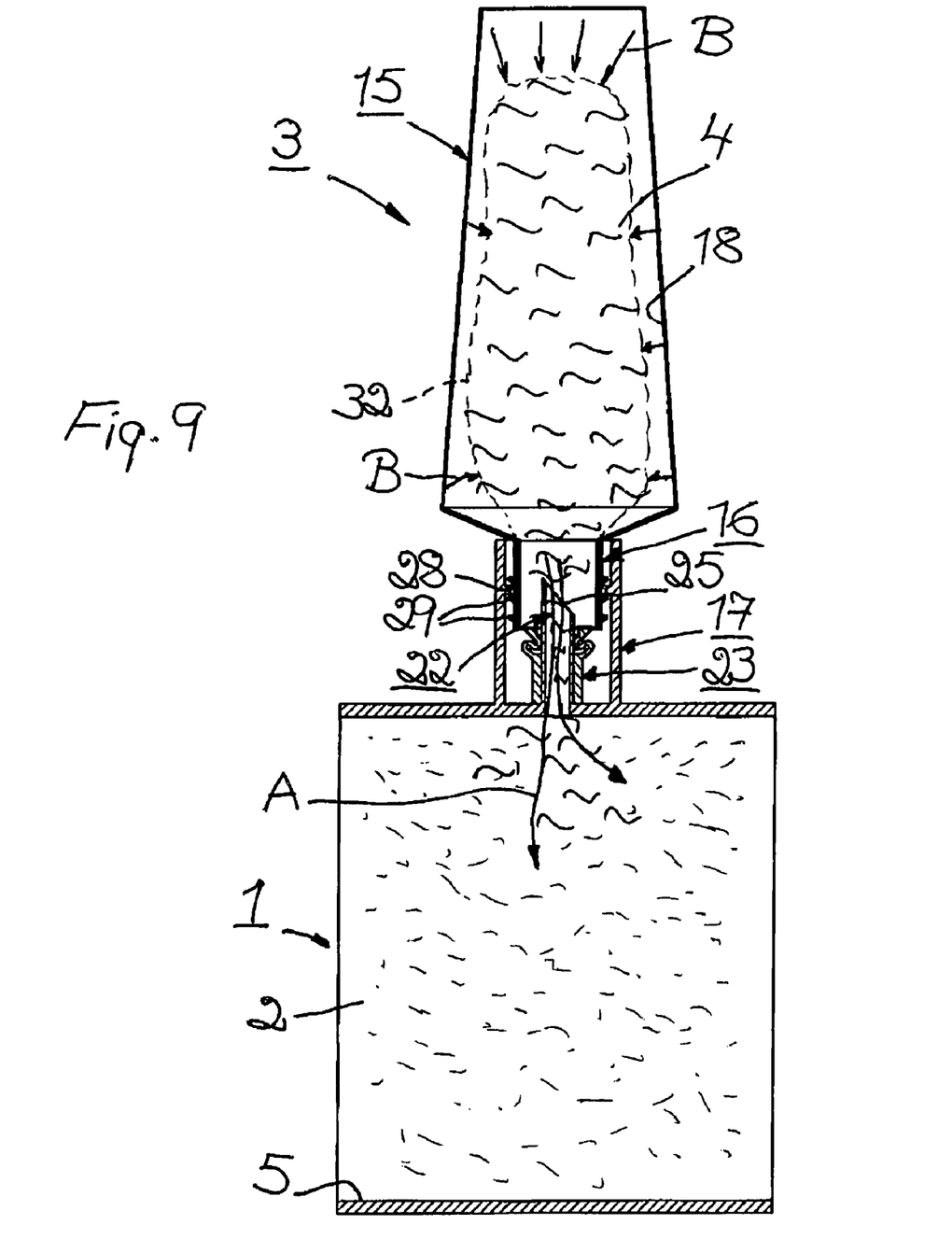

The aerosol container 15 may also be constructed in various different ways other than as described above. Thus the liquid component 4, instead of being, as in FIGS. 2 and 3 and in FIGS. 4, 5 and 6, in the same space 18 in the aerosol container 15 as the propellant gas (arrows B in FIGS. 4, 5 and 6), may be contained in a separate flexible liquid component container 32 situated in the aerosol container, as illustrated in FIGS. 7, 8 and 9, while the propellant gas (arrows B) is outside the liquid component container in the space 18 and acts upon it from outside in order to push the liquid component out of it. Accordingly, in this embodiment, the liquid component container 32 is provided with or connected to the connecting element 16 in order to connect the aerosol container 15 to the connecting element 17 on the bone cement mixer 1 so that the liquid component 4 is pushed out of the liquid component container into the mixing space 5 by the propellant gas.

Figure 1:
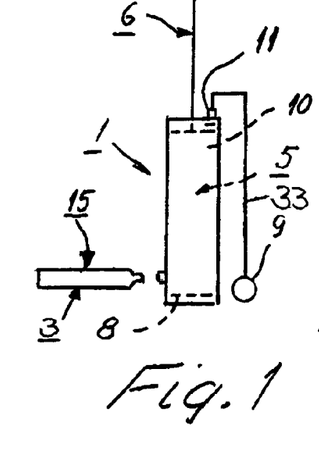
FIG. 1 depicts a liquid container in side view beside a bone cement mixer to which the container is to be connected.
Figure 10:
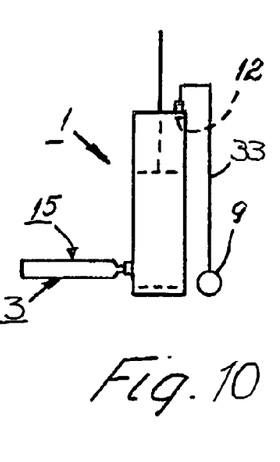
FIG. 10 depicts the liquid container according to FIG. 1 in an empty state and connected to the bone cement mixer.
Figure 12:
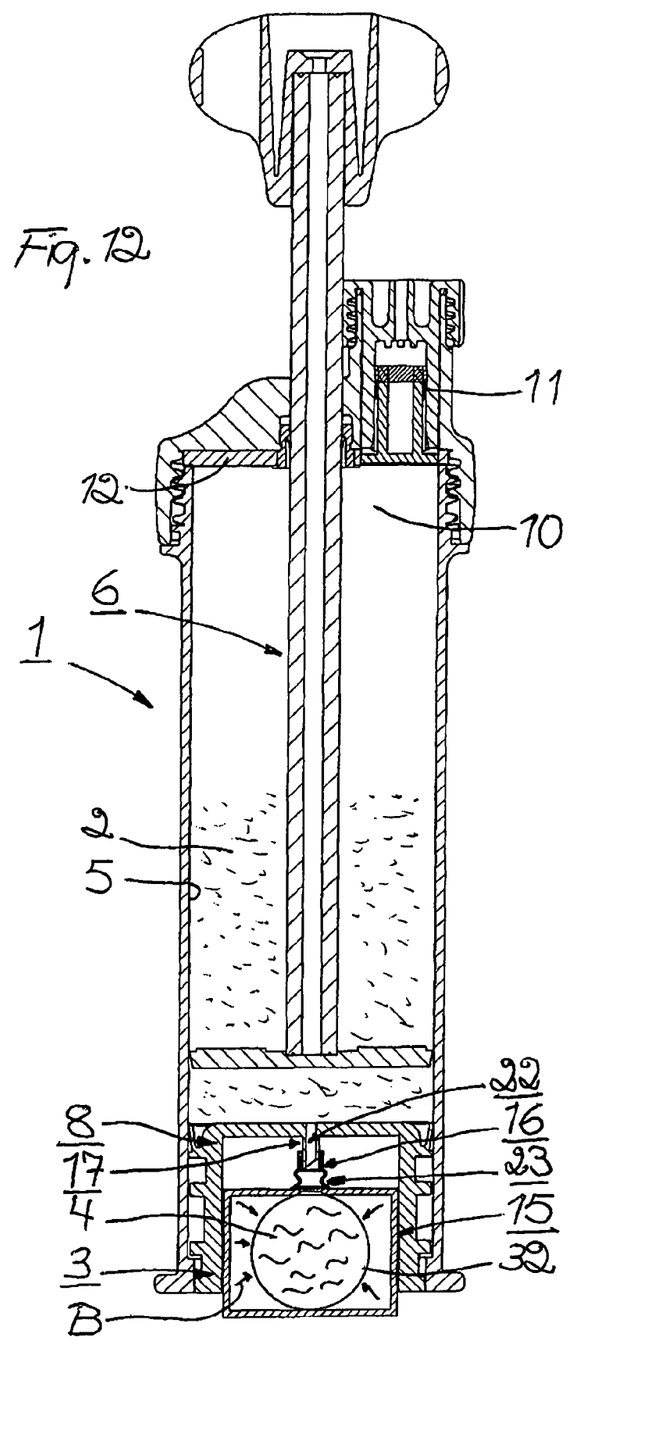
FIG. 12 depicts in section an alternative location of the connecting element on the bone cement mixer.

If the aerosol container 15 is intended to be used in association with a bone cement mixer 1 with a delivery piston 8, as in FIGS. 1, 10 and 11, it may alternatively be connected to the delivery piston, as illustrated by FIG. 12, which in that case is provided with a suitable type of connecting element 17 which fits to the connecting element 16 of the aerosol container, whereby the connecting elements 16, 17 together form a joint, e.g. of a kind similar to that described above, with suitable opening means 22 and a suitable seal 23.

As depicted in FIG. 12, the connecting element 17 on the delivery piston 8 is oriented in the latter's movement direction so that the connecting element 16 of the aerosol container 15 can be connected to it on the opposite side of the delivery piston from the mixing space 5. The aerosol container 15 in FIG. 12 is substantially cylindrical and closed, and comprises, as in FIGS. 7 to 9, an inner flexible liquid component container 32 surrounded by the propellant gas, but it may of course be of any other suitable configuration.

The invention is not limited to the preferred embodiment described above and depicted in the drawings but may be varied within the scopes of the claims set out below. As examples of undepicted embodiments, it may be mentioned that the connecting elements 16, 17 may be configured and/or positioned in some other way, the opening means 22 may be configured and/or positioned in some other way and the bone cement mixer 1 may be configured in some other way. The powder and liquid components 2, 4 may possibly be components other than a polymer and a monomer respectively.

The invention claimed is:

1. A device at a bone cement mixer, wherein:
   the bone cement mixer (1) comprises at least one mixing space (5) for mixing of powder and liquid components (2, 4) to make bone cement,
   the powder component (2) is placed in the mixing space (5) and the liquid component (4) in a liquid container (3), and
   the liquid component (4) can be transferred from the liquid container (3) to the mixing space (5) and the powder component (2) placed therein,
   the liquid container (3) is an aerosol container (15) and contains, in addition to the liquid component (4), a propellant gas for pushing the liquid component (4) out from the aerosol container (15) into the mixing space (5),
   the aerosol container (15) has a connecting element (16) with a closing wall (21) which closes the aerosol container (15),
   the aerosol container (15) is adapted to being opened when it is connected to a corresponding connecting element (17) on the bone cement mixer (1),
   the connecting element (17) of the bone cement mixer (1) has a seal (23) which closes the mixing space (5) of the bone cement mixer (1) and an opening means (22) which, when the connecting element (16) of the aerosol container (15) is connected to the connecting element (17) of the bone cement mixer (1), uses a single end to push up first a hole in the seal (23) and then in the closing wall (21) in the connecting element (16) of the aerosol container (15), such that the propellant gas in the aerosol container (15) can push the liquid component (4) out from the space (18) in the aerosol container (15) and into the mixing space (5), and
   the aerosol container (15) being connectable to a bone cement mixer (1) which has a delivery means (8) in the form of a piston which is anchorable relative to the bone cement mixer (1) and which can be released from the latter after the mixing of the powder and liquid components (2, 4), so that the delivery piston (8) can move and/or be moved relative to the mixing space (5) of the bone cement mixer (1), the connecting element (17) of the bone cement mixer (1) being disposed on the delivery piston (8) to mechanically connect the bone cement mixer (1) to the aerosol container (15) wherein the opening means push in the same direction through the seal (23) and the closing wall (21).

2. A device according to claim 1, wherein the aerosol container (15) is made of plastic material which prevents the liquid component (4) from escaping from it.

3. A device according to claim 1, wherein the aerosol container (15) is made of aluminum or an aluminum alloy, which prevents the liquid component (4) from escaping from it.

4. A device according to claim 1, wherein the aerosol container (15) is made of glass which prevents the liquid component (4) from escaping from it.

5. A device according to claim 1, wherein the connecting element (16) of the aerosol container (15) and the corresponding connecting element (17) on the bone cement mixer (1) together form a threaded joint.

6. A device according to claim 5, wherein the connecting element (16) of the aerosol container (15) has threads (19) so that it can be screwed firmly to threads (20) on the corresponding connecting element (17) on the bone cement mixer (1).

7. A device according to claim 1, wherein the connecting element (16) of the aerosol container (15) and the corresponding connecting element (17) on the bone cement mixer (1) together form a snap joint.

8. A device according to claim 7, wherein the connecting element (17) of the bone cement mixer (1) has a flange (28) pointing radially inwards which can be snapped firmly into a groove (30) delineated between flanges (29) which point radially outwards on the corresponding connecting element (16) on the aerosol container (15).

9. A device according to claim 1, wherein the connecting element (16) of the aerosol container (15) and the corresponding connecting element (17) on the bone cement mixer (1) together form a bayonet joint.

10. A device according to claim 1, wherein the propellant gas in the aerosol container (15) pushes the liquid component (4) out from the space (18) in the aerosol container (15), past or through the opening means (22), and into the mixing space (5).

11. A device according to claim 10, wherein the opening means (22) is disposed in and integrally formed with the connecting element (17) of the bone cement mixer (1).

12. A device according to claim 1, wherein the opening means (22) takes the form of a cannula (25) and the seal (23) takes the form of a rubber socket (26) which is placed over the cannula (25), whereby the cannula (25) pushes up first a hole in a sealing wall (31) of the rubber socket (26) and thereafter a hole in the closing wall (21) of the connecting element (16) of the aerosol container (15) when the connecting element (16) of the aerosol container (15) is connected to the connecting element (17) of the bone cement mixer (1).

13. A device according to claim 1, wherein the aerosol container (15) is connectable to a bone cement mixer (1) which has at least one mixing means (6) for mixing the powder and liquid components (2, 4).

14. A device according to claim 1, wherein the aerosol container (15) is connectable to a bone cement mixer (1) which has means (11) for connection to a vacuum source (9) adapted to generating vacuum in the mixing space (5) of the bone cement mixer (1).

15. A device according to claim 14, wherein the vacuum source (9) is adapted to generating vacuum in the mixing space (5) during mixing of the powder and liquid components (2, 4) and to maintaining that vacuum during accumulation of ready-mixed bone cement in a delivery portion (10) of the mixing space (5), from which delivery portion (10) accumulated bone cement is to be delivered.

16. A device according to claim 14, wherein the aerosol container (15) is connectable to a bone cement mixer (1) which has at least one filter (12) for preventing the powder and liquid components (2, 4) and/or bone cement from being sucked out from the mixing space (5) by the vacuum source (9).

17. A device according to claim 1, wherein the delivery piston (8) can be released from the bone cement mixer (1) and is adapted to delivering ready-mixed bone cement from the mixing space (5).

18. A device according to claim 1, wherein the delivery piston (8) can be released and be sucked into the mixing space (5) by vacuum in the latter and is adapted to accumulating ready-mixed bone cement in a delivery portion (10) of the mixing space (5).

19. A device according to claim 1, wherein the connecting element (17) on the delivery piston (8) is oriented in the movement direction of the delivery piston (8) so that the connecting element (16) of the aerosol container (15) can be secured thereto on the opposite side of the delivery piston (8) from the mixing space (5).

20. A device according to claim 1, wherein the mixing space (5) is elongate and that the connecting element (17) of the bone cement mixer (1) is disposed radially relative to the longitudinal axis of the mixing space (5).

21. A device according to claim 1, wherein:
the liquid component (4) in the aerosol container (15) is enclosed in a liquid component container (32) situated in the aerosol container (15), whereas the propellant gas is situated outside the liquid component container (32) and acts upon it from outside in order to push the liquid component (4) out from it, and
the liquid component container (32) is provided with or connected to said connecting element (16) for connecting the aerosol container (15) to the connecting element (17) on the bone cement mixer (1) so that the liquid component (4) is pushed out from the aerosol container (15) into the mixing space (5) by said propellant gas.

22. A device according to claim 6, wherein the connecting element (16) of the aerosol container (15) is cylindrical and has outside threads (19) so that it can be screwed firmly to inside threads (20) on the corresponding cylindrical connecting element (17) on the bone cement mixer (1).

23. A device according to claim 1, wherein the opening means (22) is positioned axially between the seal (23) and the mixing space (5) prior to pushing up a hole in the seal (23).

24. A device according to claim 1, wherein the seal (23) covers the opening means (22) to enclose the opening means (22) within the bone cement mixer (1).

25. A device according to claim 1, wherein, as the aerosol container (15) is being connected to the connecting element (17), the aerosol container (15) engages the seal (23) and pushes the seal (23) into engagement with the opening means (22) in order to open the seal (23) with the opening means (22) prior to the opening means (22) opening the aerosol container (15).

26. A device according to claim 1, wherein the opening means (22) opens the seal (23) and the aerosol container (15) in the same direction.

27. A device according to claim 1, wherein the opening means (22) extends away from the mixing space (5) for opening the seal (23) and the aerosol container (15).

28. A device according to claim 1, wherein the connecting element (22) of the bone cement mixer (1) engages the connecting element (16) of the aerosol container (15) to mechanically connect the bone cement mixer (1) to the aerosol container (15).

29. A device according to claim 1, wherein the mechanical connection between the bone cement mixer (1) and the aerosol container (15) is one ot a threaded connection and a bayonet joint.

* * * * *